(12) United States Patent
McQueen

(10) Patent No.: US 10,286,248 B2
(45) Date of Patent: May 14, 2019

(54) VIEWING NECK POSTURE DISCOMFORT RELIEF ACCESSORY

(71) Applicant: Harold McQueen, Seymour, IN (US)

(72) Inventor: Harold McQueen, Seymour, IN (US)

( * ) Notice: Subject to any disclaimer, the term of this patent is extended or adjusted under 35 U.S.C. 154(b) by 26 days.

(21) Appl. No.: 15/681,367

(22) Filed: Aug. 19, 2017

(65) Prior Publication Data

US 2019/0054341 A1 Feb. 21, 2019

(51) Int. Cl.
| | |
|---|---|
| *G02B 21/00* | (2006.01) |
| *A63B 21/00* | (2006.01) |
| *G02C 3/00* | (2006.01) |
| *A63B 23/025* | (2006.01) |
| *A61B 5/00* | (2006.01) |
| *G02B 17/06* | (2006.01) |

(52) U.S. Cl.
CPC ........ *A63B 21/4003* (2015.10); *A63B 23/025* (2013.01); *G02C 3/006* (2013.01); *A61B 5/6803* (2013.01); *G02B 17/06* (2013.01)

(58) Field of Classification Search
CPC ........ G02B 5/08; G02B 17/00; G02B 17/002; G02B 17/02; G02B 17/023; G02B 17/026; G02B 17/06; G02B 23/00; G02B 23/02; G02B 23/08; G02B 23/125; G02B 23/18; G02B 27/02; G02B 27/021; G02B 27/022; G02B 27/024
USPC ....... 359/362, 363, 367, 480, 482, 838, 850, 359/855, 856, 857, 860, 861, 865, 871, 359/402, 403, 404
See application file for complete search history.

(56) References Cited

U.S. PATENT DOCUMENTS

| | | | | |
|---|---|---|---|---|
| 5,422,759 A | * | 6/1995 | Lee | G02B 17/02 359/840 |
| 5,760,865 A | * | 6/1998 | Webster | G02B 27/144 351/41 |
| 6,280,031 B1 | * | 8/2001 | Zerkle | G02B 5/04 351/155 |
| 9,690,119 B2 | * | 6/2017 | Garofolo | G02C 7/14 |
| 2016/0363775 A1 | * | 12/2016 | Snider | G02B 27/08 |
| 2017/0199387 A1 | * | 7/2017 | Koch, III | G02B 27/022 |

* cited by examiner

*Primary Examiner* — Arnel C Lavarias
(74) *Attorney, Agent, or Firm* — The Iwashko Law Firm, PLLC; Lev Ivan Gabriel Iwashko

(57) ABSTRACT

A viewing neck posture discomfort relief accessory includes a user wearable head band assembly, and an optical assembly attached to the user wearable head band assembly. The user wearable head band assembly is worn by the user to place the optical assembly in front of the user's eyes. The optical assembly enables the user to look into the optical assembly in a forward direction so that the neck of the user can be held in a generally upright comfortable posture due to the optical assembly having pairs of mirrors that reflect the path of sight of the user' eyes from the forward direction to a downward direction to allow viewing an item, such as a book page or mobile device keyboard or screen, being held by the user in a generally horizontal orientation.

13 Claims, 2 Drawing Sheets

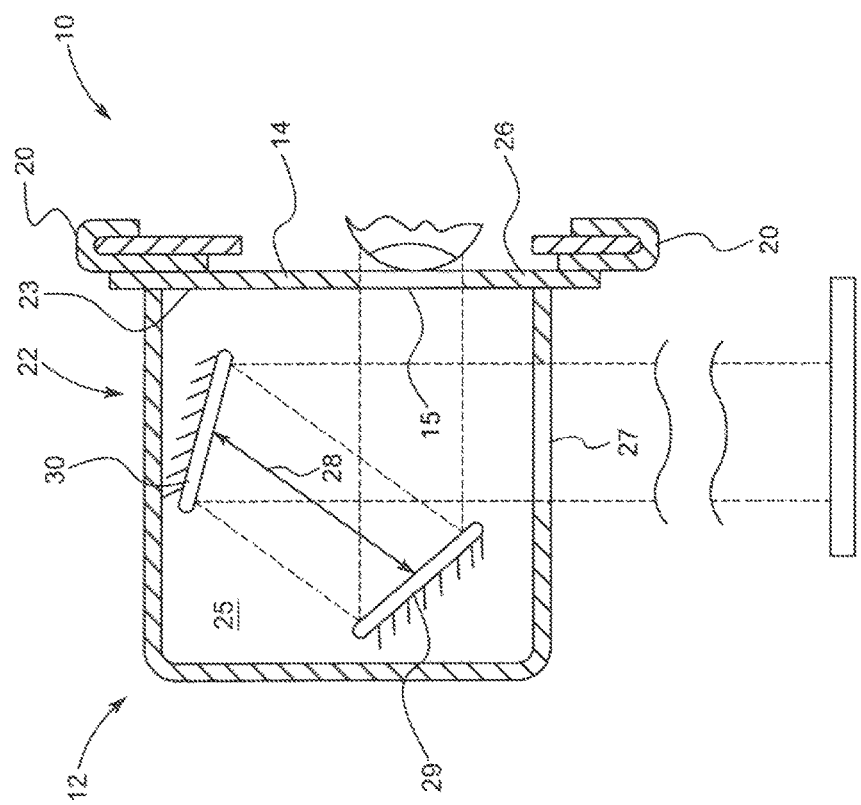

VIEWING NECK POSTURE DISCOMFORT RELIEF ACCESSORY

BACKGROUND OF THE INVENTION

1. Field of the Invention

The present general inventive concept relates generally to avoidance of neck strains frequently caused by the viewing posture a user assumes while reading a book or working on a mobile device and, more particularly, is concerned with a viewing neck posture discomfort relief accessory.

2. Description of the Related Art

Reading a book and working on a mobile device are common pastimes which many people find enjoyable. A serious problem which frequently arises, however, is that the neck of a person often has to be bent somewhat forward and downward to order for the person to read the book or work on mobile device. This constant bending of the neck can cause tension and strain to the neck muscles which, after an extended period of time, can take the pleasure out of reading the book and working on the mobile device. Thus, there remains a need for a practical device that will enable a person to avoid common neck aches from discomforting neck postures being maintained over extended periods of time while reading a book or working on a mobile device.

The present general inventive concept described herein provides a viewing neck posture discomfort relief accessory adapted to protect readers of books and users of mobile devices from needing to bend their necks into straining and discomforting postures to order to view the horizontally disposed book and mobile device. Primary components in Applicant's viewing neck posture discomfort relief accessory are a user wearable head band assembly and an optical assembly held by the user wearable head band assembly in front of the eyes of the user. The optical assembly reflects the user path of sight from a forward direction to a downward direction rather than bending the neck of the user away from a comfortable posture. The viewing neck posture discomfort relief accessory of the present general inventive concept conveniently enables users to decouple the viewing enjoyment of reading books and working on mobile devices from the necessity of assuming unhealthy neck postures. As a result, potentially serious maladies commonly incurred by book readers and mobile device users may be avoided.

SUMMARY

The present general inventive concept provides a viewing neck posture discomfort relief accessory.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a viewing neck posture discomfort relief accessory, including a user wearable head band assembly, and an optical assembly attached to the user wearable head band assembly. When the user wearable head band assembly is worn by the user to place the optical assembly in front of the user's eyes, the optical assembly enables the user to look into the optical assembly in a forward direction so that the neck of the user can be held in a generally upright comfortable posture due to the optical assembly reflecting the path of sight of the user from the forward direction to a downward direction to allow viewing an item, such as a book page or mobile device keyboard or screen, being held by the user in a generally horizontal orientation.

The user wearable head band assembly may have a head band to fit about the head of the user and a mounting platform coupled to the head band so as to overlie the eyes and area of the head of the user about the eyes.

The mounting platform of the user wearable head band assembly may have viewing windows horizontally spaced apart from one another to accommodate alignment with the eyes of the user, and an inwardly arched cutout spaced from and located between the viewing windows to accommodate receiving the nose of the user through the inwardly arched cutout.

The mounting platform may also have a soft nose piece fitted along the inwardly arched cutout of the counting platform.

The mounting platform may also have downwardly projecting lights supported along lower edge portions of the mounting platform being spaced apart by the inwardly arched cutout of the mounting platform.

The user wearable head band assembly may also have a pair of couplers supported about a periphery of the mounting platform and being configured to fit against the area of the head of the user about the eyes or upon front portions of an eyeglass lens frame.

The optical assembly may have a housing supported at a forward side of the mounting platform that faces away from the head of the user, the housing having a pair of housing portions that have respective cavities that are open at least at respective rear and lower sides and surround respective viewing windows through the mounting platform.

The optical assembly may also have two pairs of mirrors of predetermined configurations with each pair being adjustably mounted within one of the housing portions of the optical assembly housing and including a lower mirror and an upper mirror disposed in predetermined positional and adjustable angular relationships to each other, to the respective viewing windows in the mounting platform and thus to the eyes of the user, and to the open lower sides of the housing portions.

The predetermined configurations of the mirrors are planar in shape. The positional relationships of the mirrors of each pair includes the lower mirror placed below and forward of the upper mirror with both displaced forward from the mounting platform, the upper mirror pieced above and aligned with the open lower side of each housing portion, and the lower mirror aligned with a respective one of the viewing windows. In an exemplary embodiment, the adjustable angular relationships of the mirrors of each pair to each other includes the lower mirror rotated counterclockwise to a position at an angle of sixty degrees relative to a horizontal direction and the upper mirror rotated clockwise to a position at an angle of sixty degrees relative to a vertical direction.

BRIEF DESCRIPTION OF DRAWINGS

FIG. 2 is a side elevation view of the viewing neck posture discomfort relief accessory of FIG. 1, showing in a dashed line form the bending of a user line of sight by an optical assembly of the accessory.

DETAILED DESCRIPTION OF THE INVENTION

Figure 1:
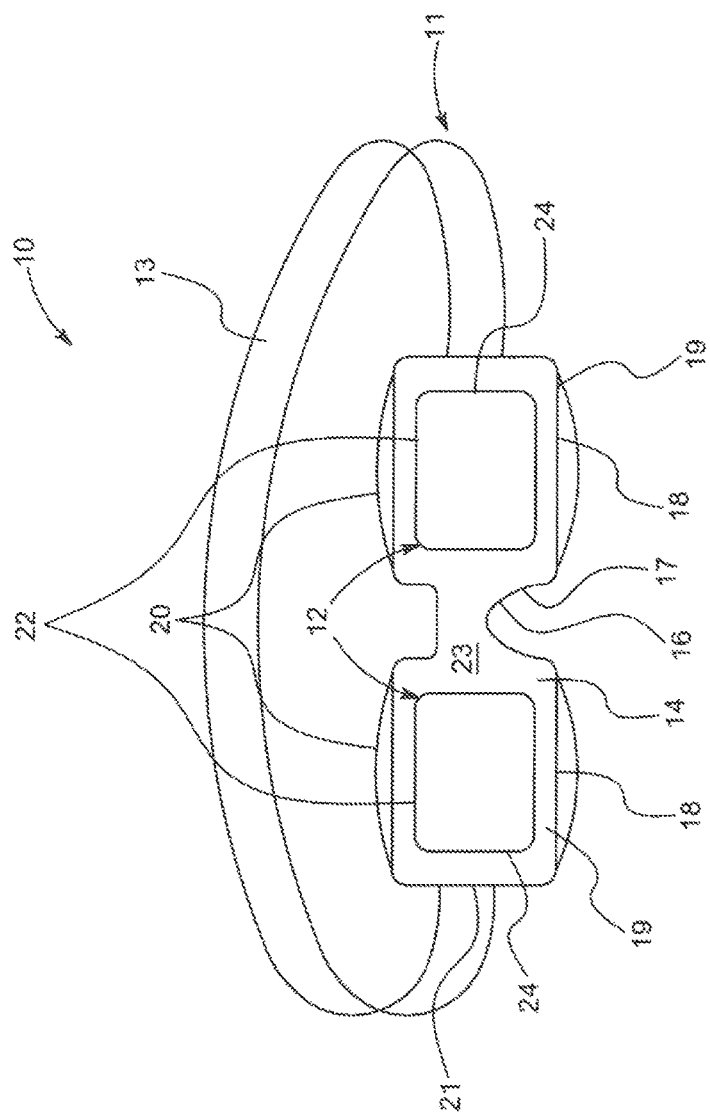
FIG. 1 is a front perspective view of a viewing neck posture discomfort relief accessory built in accordance with the present general inventive concept.

Referring now to FIGS. 1 and 2 of the drawings, a user viewing neck posture discomfort relief accessory 10 (hereinafter for the sake of brevity being referred to as the "user viewing accessory 10") is illustrated having a user wearable head band assembly 11 and an optical assembly 12 attached to the user wearable head band assembly 11. When the user wearable head band assembly 11 is worn by a user to place the optical assembly 12 in front of the user's eyes E, the optical assembly 12 enables the user to look into the optical assembly 12 in a forward direction so that the neck of the user can be held in a generally upright comfortable posture due to the optical assembly 12 reflecting the path of sight POS of the user from the forward direction to a downward direction to allow viewing an item I, such as a book page or mobile device keyboard or screen being held by the user, in a generally horizontal orientation.

The user wearable head band assembly 11 of the user viewing assembly 10 may include a head band 13 adapted to fit about the head of the user (not shown), and a mounting platform 14 coupled to the head band 13 so as to overlie the eyes E and area of the head of the user about the eyes. The mounting platform 14 may have a pair of viewing windows 15 horizontally spaced apart from one another to accommodate alignment with the eyes E of the user, and an inwardly arched cutout 16 spaced from and located between the viewing windows 15 to accommodate receiving the nose of the user (not shown) through the inwardly arched cutout 16. The mounting platform 14 may also have a soft nose piece 17 fitted along the inwardly arched cutout 16 of the mounting platform 14, and a pair of downwardly projecting lights 18, especially for night time use, being supported along lower edge portions 19 of the mounting platform 14 and being spaced apart by the inwardly arched cutout 16. The user wearable head band assembly 11 may also have a pair of couplers 20 supported about a periphery 21 of the mounting platform 14 and being configured to fit against the area of the head of the user about the eyes or upon front portions of an eyeglass lens frame F.

The optical assembly 12 of the user viewing assembly 10 may include a housing 22 supported at a forward side 23 of the mounting platform 14 that faces away from the head of the user. The housing 22 may be in the form of a pair of housing portions 24 each having a respective cavity 25 that is open at least at respective rear and lower sides 26, 27 and surround the respective one of the viewing windows 15 formed through the mounting platform 14. The optical assembly 12 may also have two pairs of mirrors 28 of predetermined configurations with each pair being adjustably mounted within one of the housing portions 24 of the optical assembly housing 22. Each mirror pair 28 includes a lower mirror 29 and an upper mirror 30 disposed in predetermined positional and adjustable angular relationships to each other, to the respective viewing windows 15 in the mounting platform 14 and thus to the eyes of the user, and to the open lower sides 27 of the housing portions 24.

The predetermined configurators of the mirrors 29, 30 are planar in shape. The positional relationships of the mirrors of each mirror pair 28 includes the lower mirror 29 placed below and forward of the upper mirror 30 with both displaced forward from the mounting platform 14, the upper mirror 30 above and aligned with the open lower side 27 of each housing portion 24, and the lower mirror 29 aligned with the respective one of the viewing windows 15. In one exemplary embodiment, the adjustable angular relationships of the mirrors of each mirror pair 28 to each other includes the lower mirror 29 rotated counterclockwise to a position at an angle of sixty degrees relative to the horizontal direction H and the upper mirror 30 rotated clockwise to a position at an angle of sixty degrees relative to the vertical direction V.

In light of the foregoing description, it will be readily understood that a primary purpose of the user viewing accessory 10 is to provide a device able to avoid neck strains caused by viewing horizontally oriented items, such during reading books or working on mobile devices. Whereas enjoying a book is a common pastime for many individuals, users without the benefit of the user viewing accessory 10 often have to position their neck downwards to view the horizontally oriented item. This constant bending can cause tension to the neck muscles, after an extended period of time, taking the joy out of reading. The user viewing accessory 10 allows users to view (work or read) while looking forward, eliminating common neck aches created from discomforting reading postures. Simple to use, consumers will wear the user viewing accessory 10 similar to goggles, by placing the head band 13 over their heads to stay put while aligning the pair of couplers with their eyes; once on, individuals can hold reading materials as per usual, enabling the mirrors of the optical assembly 12 to reflect the text into the eyes of the user, granting a perfect vantage point for reading the words without bending the neck. Also, with the pair of downwardly projecting lights 18 located under the optical assembly 12 the horizontally oriented items may be seen clearly even when in poorly lit areas.

Although a few embodiments of the present general inventive concept have been shown and described, it will be appreciated by those skilled in the art that changes ma be made in these embodiments without departing from the principles and spirit of the general inventive concept, the scope of which is defined in the appended claims and their equivalents.

What is claimed is:

1. A viewing neck posture discomfort relief accessory, comprising:
   a user wearable head band assembly, comprising:
      a head band to fit about a head of a user,
      a mounting platform coupled to the head band so as to overlie eyes of the user and an area of the head of the user about the eyes of the user, and
      a pair of couplers supported about a periphery of the mounting platform and being configured to fit against the area of the head of the user about the eyes or upon front portions of an eyeglass lens frame; and
   an optical assembly attached to the head band assembly such that when the head band assembly is worn by the user the optical assembly is placed in front of the eyes of the user,
   wherein the optical assembly is configured to enable the user to look into the optical assembly in a forward direction so that a neck of the user can be held in a generally upright comfortable posture due to the optical assembly reflecting a path of sight of the eyes of the user from a forward direction to a downward direction to allow viewing an item being held in a horizontal orientation.

2. The accessory of claim 1, wherein the mounting platform of the user wearable head band assembly includes a pair of viewing windows horizontally spaced apart from one another to accommodate alignment with the eyes of the user.

3. The accessory of claim 2, wherein the mounting platform of the user wearable head band assembly also includes an inwardly arched cutout spaced from and located between the viewing windows to accommodate receiving a nose of the user through the inwardly arched cutout.

4. The accessory of claim 3, wherein the mounting platform of the user wearable head band assembly also includes a soft nose piece fitted along the inwardly arched cutout of the mounting platform.

5. The accessory of claim 3, wherein the mounting platform of the user wearable head band assembly also includes downwardly projecting lights supported along lower edge portions of the mounting platform being spaced apart by the inwardly arched cutout of the mounting platform.

6. A viewing neck posture discomfort relief accessory, comprising:
   a user wearable head band assembly, comprising:
      a head band to fit about a head of a user, and
      a mounting platform coupled to the head band so as to overlie eyes of the user and an area of the head of the user about the eyes of the user; and
   an optical assembly attached to the head band assembly such that when the head band assembly is worn by the user the optical assembly is placed in front of the eyes of the user,
   wherein the optical assembly is configured to enable the user to look into the optical assembly in a forward direction so that a neck of the user can be held in a generally upright comfortable posture due to the optical assembly reflecting a path of sight of the eyes of the user from a forward direction to a downward direction to allow viewing an item being held in a horizontal orientation, and
   wherein the optical assembly comprises a housing supported at a forward side of the mounting platform of the user wearable head band assembly that faces away from the head of the user, the housing having a pair of housing portions that have respective cavities that are open at least at respective rear and lower sides and surround respective viewing windows through the mounting platform.

7. The accessory of claim 6, wherein the optical assembly also comprises two pairs of mirrors of predetermined configurations with each pair being adjustably mounted within one of the housing portions of the housing.

8. The accessory of claim 7, wherein the predetermined configurations of the mirrors are planar in shape.

9. The accessory of claim 6, wherein the optical assembly also comprises two pairs of mirrors with each pair of mirrors within one of the housing portions including a lower mirror and an upper mirror disposed in predetermined positional relationship to each other, to the respective viewing windows in the mounting platform and thus to the eyes of the user, and to the open lower sides of the housing portions.

10. The accessory of claim 9, wherein the predetermined positional relationships of the mirrors of each pair Includes the lower mirror placed below and forward of the upper mirror with both lower and upper mirrors displaced forward from the mounting platform, the upper mirror being above and aligned with the open lower side of the respective housing portion, and the lower mirror being aligned with a respective one of the viewing windows.

11. The accessory of claim 6, wherein the optical assembly also comprises two pairs of mirrors with each pair of mirrors within one of the housing portions including a lower mirror and an upper mirror disposed in predetermined adjustable angular relationships to each other, to the respective viewing windows in the mounting platform and thus to the eyes of the user, and to the open lower sides of the housing portions.

12. The accessory of claim 11, wherein the angular relationships of the mirrors of each pair to each other includes the lower mirror rotated counterclockwise to a position at an angle of sixty degrees relative to a horizontal direction and the upper mirror rotated clockwise to a position at an angle of sixty degrees relative to a vertical direction.

13. A viewing neck posture discomfort relief accessory, comprising:
   a user wearable head band assembly, comprising:
      a head band to fit about a head of a user,
      a mounting platform coupled to the head band so as to overlie eyes of the user and an area of the head of the user about the eyes of the user, and
      a pair of couplers supported about a periphery of the mounting platform to fit against the area of the head of the user about the eyes or upon front portions of an eyeglass lens frame; and
   an optical assembly attached to the head band assembly such that when the head band assembly is worn by the user, the optical assembly is placed in front of the eyes of the user to allow a user to view an object held below the eyes of the user when the eyes of the user are looking in a forward direction.

* * * * *